US009580381B2

(12) United States Patent
Kasemi et al.

(10) Patent No.: US 9,580,381 B2
(45) Date of Patent: Feb. 28, 2017

(54) AMINE FOR LOW-EMISSION EPOXY RESIN PRODUCTS

(71) Applicant: Sika Technology AG, Baar (CH)

(72) Inventors: Edis Kasemi, Zurich (CH); Andreas Kramer, Zurich (CH); Ursula Stadelmann, Zurich (CH); Urs Burckhardt, Zurich (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

(21) Appl. No.: 14/759,511

(22) PCT Filed: Dec. 20, 2013

(86) PCT No.: PCT/EP2013/077704
§ 371 (c)(1),
(2) Date: Jul. 7, 2015

(87) PCT Pub. No.: WO2014/108306
PCT Pub. Date: Jul. 17, 2014

(65) Prior Publication Data
US 2015/0344406 A1    Dec. 3, 2015

(30) Foreign Application Priority Data

Jan. 8, 2013 (EP) .................................... 13150534

(51) Int. Cl.
C07C 211/00 (2006.01)
C09K 3/00 (2006.01)
C07C 211/27 (2006.01)
C07C 209/24 (2006.01)
C08G 59/22 (2006.01)
C08G 59/50 (2006.01)
C08G 59/56 (2006.01)
C08L 63/00 (2006.01)

(52) U.S. Cl.
CPC .......... *C07C 211/27* (2013.01); *C07C 209/24* (2013.01); *C08G 59/223* (2013.01); *C08G 59/50* (2013.01); *C08G 59/5033* (2013.01); *C08G 59/5046* (2013.01); *C08G 59/56* (2013.01); *C08L 63/00* (2013.01)

(58) Field of Classification Search
CPC ..... C07C 211/27; C07C 209/24; C08G 59/56; C08G 59/50; C08G 59/223; C08G 59/5046; C08G 59/5033; C08L 63/00
USPC ...................... 525/103; 252/182.23; 564/388
See application file for complete search history.

(56) References Cited

U.S. PATENT DOCUMENTS

| 2,891,039 | A | * | 6/1959 | Kolb | ..................... C08F 236/04 526/318 |
| 3,598,782 | A | * | 8/1971 | Beckmanet | ............... C08K 5/17 524/100 |
| 5,426,157 | A | | 6/1995 | Starner et al. | |
| 5,739,209 | A | | 4/1998 | Lassila et al. | |
| 5,902,586 | A | * | 5/1999 | Jennings | ............ A61K 39/0258 424/178.1 |
| 2002/0055605 | A1 | | 5/2002 | Yonehama et al. | |
| 2010/0048827 | A1 | | 2/2010 | Walker et al. | |

FOREIGN PATENT DOCUMENTS

| CN | 101781397 A | 7/2010 |
| EP | 1 188 740 A2 | 3/2002 |
| EP | 2 159 218 A1 | 3/2010 |

OTHER PUBLICATIONS

Notification of Transmittal of Translation of the International Preliminary Report on Patentability (Forms PCT/IB/373 and PCT/ISA/237) issued on Jul. 23, 2015, by the International Bureau of WIPO in corresponding International Patent Application No. PCT/EP2013/077704. (7 pages).
International Search Report (PCT/ISA/210) mailed on Mar. 25, 2014, by the European Patent Office as the International Searching Authority for International Application No. PCT/EP2013/077704.
Written Opinion (PCT/ISA/237) mailed on Mar. 25, 2014, by the European Patent Office as the International Searching Authority for International Application No. PCT/EP2013/077704.
Chinese Office Action issued in corresponding Chinese Patent Application No. 201380065721.4 issued Jun. 6, 2016.

* cited by examiner

*Primary Examiner* — David Karst
(74) *Attorney, Agent, or Firm* — Buchanan Ingersoll & Rooney PC

(57) ABSTRACT

An amine which can be used in epoxy resin compositions that cure at room temperature. The amine dilutes the composition highly effectively, allows rapid, trouble-free curing, even in cold and damp conditions, and reduces brittleness. The amine is particularly suitable as a constituent of a curing agent for low-emission epoxy resin compositions that cure at room temperature, in particular for floor coverings.

7 Claims, No Drawings

AMINE FOR LOW-EMISSION EPOXY RESIN PRODUCTS

TECHNICAL FIELD

The invention relates to the field of amines, curing agents for epoxy resins, epoxy resin products and their use, in particular as coatings, coverings and paints.

PRIOR ART

Epoxy resin products suitable for coating purposes should have a viscosity that is as low as possible so that they are easy to process and self-leveling at ambient temperature. Furthermore, they should cure as fast as possible and trouble-free, even in cold and damp conditions, and thereby form a flat, even surface without clouding, spots or craters. Finally, a cured coating should have high hardness with low brittleness to withstand mechanical stress as well as possible. For visually demanding applications, such as floor coverings, a coating should also have a minimum tendency to yellow when exposed to light.

To achieve these properties, typically thinners are used in epoxy resin coatings according to the prior art. The thinners improve the workability, reduce the brittleness of the coating and improve the surface quality by reducing the incidence of blushing effects. "Blushing effects" are surface defects occurring during curing such as clouding, spots, roughness and stickiness caused by salt formation ("blushing") of amines with carbon dioxide ($CO_2$) from the air, especially in the presence of high humidity and at low temperatures.

The diluents usually employed, in particular benzyl alcohol, glycols and alkyl phenols, are unreactive with epoxy resins at room temperature and are therefore not incorporated in the resin matrix during curing. Nowadays, however, low-emission products are increasingly desired, having a low content of substances that are released by evaporation or diffusion processes after curing. For low-emission epoxy resin products, non-incorporable diluents therefore can be used only in very small quantities or not at all.

Another option for diluting epoxy resins is the use of elevated levels of small primary amines in the curing component. Such amines, e.g., diethylene triamine, isophorone diamine or xylylene diamine are, however, malodorous, highly irritating to skin and eyes, and sensitizing, and often they lead to blushing effects.

U.S. Pat. No. 5,426,157 describes epoxy resin compositions containing N,N'-dimethylated diamines. U.S. Pat. No. 5,739,209 describes mono-alkylated diamines based on 2-methyl-1,5-pentanediamine as curing agents for epoxy resins having enhanced flexibility and resistance. However, the diamines described dilute low-emission epoxy coatings only insufficiently.

DESCRIPTION OF THE INVENTION

It is therefore an object of the present invention to provide an amine which can be advantageously used in low-emission epoxy resin products that cure at room temperature and which are particularly suitable for coating purposes, by diluting the epoxy resin very well, allowing rapid and trouble-free curing, and reducing brittleness of the cured resin.

Surprisingly, it was found that the amine of formula (I) solves this problem very well. It is low-odor and has low volatility, and still has very low viscosity and dilutes epoxy resin coatings surprisingly well without slowing down the cure rate too much or causing blushing effects. During curing it is incorporated into the resin matrix and contributes, at high hardness, very effectively to the reduction of brittleness. Unlike similar amines, such as 1,3-bis-(benzylaminomethyl)-benzene or 1,3-bis-(2-phenylethylaminomethyl)-benzene, it surprisingly does not cause increased yellowing of the cured coating.

The amine of formula (I) makes available curing agents for low-emission epoxy resins that cure at room temperature while meeting the requirements for eco-certification, for example according to Emicode (EC1 Plus), AgBB, DIBt, Der Blaue Engel (The Blue Angel), AFSSET, RTS (M1) and US Green Building Council (LEED), and at the same time meet high standards in terms of processing and use properties.

Further aspects of the invention are the subject matter of further independent claims. Particularly preferred embodiments of the invention are the subject matter of the dependent claims.

WAYS OF CARRYING OUT THE INVENTION

The object of the present invention is an amine of formula (I).

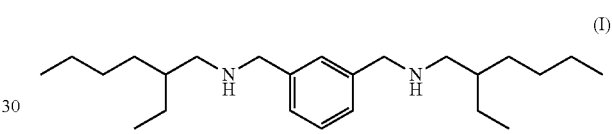

Substance names beginning with "poly" such as polyamine, polyol or polyepoxide designate substances which formally contain two or of the more functional groups that occur in their name per molecule.

"Amine hydrogen" refers to the hydrogen atoms of primary and secondary amino groups.

"Amine hydrogen equivalent weight" refers to the weight proportion of a curing agent or an amine per amine hydrogen present in the curing agent or amine.

"Non-incorporable diluent" refers to a substance that is soluble in an epoxy resin and which lowers the viscosity of the epoxy resin, but which is not covalently incorporated in the resin matrix during curing of the epoxy resin.

The term "viscosity" in this document refers to the dynamic viscosity or shear viscosity, which is defined by the ratio of shear stress and shear rate (velocity gradient), and is determined as described in the exemplary embodiments.

The amine of formula (I) is 1,3-bis-(2-ethylhexylaminomethyl)-benzene.

The amine of formula (I) can be obtained particularly advantageously by reductive alkylation of 1,3-bis-(aminomethyl)-benzene (meta-xylylene diamine or MXDA) with 2-ethyl-hexanal. The reductive alkylation can be carried out directly with molecular hydrogen or indirectly by hydrogen transfer from other reagents. Preferably, molecular hydrogen is used. Here, the conditions are advantageously selected such that on the one hand the primary amino groups are mono-alkylated with good selectivity, and on the other hand, the benzene ring is not hydrogenated.

Preferably, a hydrogen pressure of 5 to 100 bar, a temperature of 40 to 120° C. and the presence of a suitable catalyst are employed. Preferred catalysts include palladium on carbon (Pd/C), platinum on carbon (Pt/C), Adams catalyst and Raney nickel, in particular palladium on carbon and platinum on carbon.

The preparation of the amine of formula (I) by reductive alkylation in the manner described is particularly advantageous for use as a component of curing agents for epoxy resins, as primary amino groups are mono-alkylated with good selectivity, while secondary amino groups are hardly further alkylated. The product of the described method of preparation can therefore be used for curing epoxy resins in the manner described above without further work-up.

Thus, another object of the invention is a process for the preparation of the amine of formula (I) by reductive alkylation of 1,3-bis-(aminomethyl)-benzene with 2-ethylhexanal and hydrogen.

Preferably, 2-ethylhexanal and 1,3-bis-(aminomethyl)-benzene are used in a molar ratio ranging from 1.4/1 to 2.4/1, in particular 1.6/1 to 2.2/1. A molar ratio of <1.4/1 may lead to unsatisfactory results with respect to dilution effect and blushing when used in the epoxy resin curing agent, while a molar ratio >2.4/1 requires elaborate post-purification. Particularly preferred is a molar ratio of about 2/1. In this case, the amine of formula (I) can be obtained without additional work-up in high purity and as a component of epoxy resin curing agents effects excellent diluting and brittleness-reducing effects.

Particularly preferred is further a molar ratio of about 1.6/1 In addition to the amine of formula (I), the resulting reaction mixture also contains considerable fractions of N-2-ethylhexyl-1,3-bis-(aminomethyl)-benzene. As a component of epoxy resin curing agents it has a good diluting effect, a moderate brittleness-reducing effect and enables particularly fast curing.

The amine of formula (I) can be obtained in ways other than by reductive alkylation, in particular by reaction of 1,3-bis-(aminomethyl)-benzene with 2-ethylhexyl chloride or 2-ethylhexyl bromide in an appropriate ratio. This results in reaction mixtures which typically have a significant proportion of doubly alkylated amino groups.

The amine of formula (I) is a low-volatility, low-odor substance that has very low viscosity. It has such a low reactivity with $CO_2$ that—in contrast to many amines known from the prior art—it does not tend to form crusts nor does it tend to precipitate or increase viscosity when exposed to air. It shows excellent compatibility with other amines and with epoxy resins. Despite the presence of the aromatic ring, surprisingly, it does not result in increased yellowing on exposure to light in the cured epoxy resin.

Another object of the invention is the use of the amine of formula (I) as a diluent, in particular in curing agents for epoxy resins.

The amine of formula (I) has a comparatively high amine hydrogen equivalent weight. As a result, considerable quantities thereof can be used in and dilute curing agents for epoxy resins without affecting the curing reaction too greatly.

In the case of curing agents for epoxy resins having a high viscosity, for example, having a viscosity at 20° C. above 500 mPa·s, in particular above 1,000 mPa·s, the amine of formula (I) is able to reduce the viscosity of such epoxy resins considerably.

By using the amine of formula (I) as a diluent, low viscosity curing agents for epoxy resins are available which are entirely free from non-incorporable diluents and thus make possible low-emission epoxy resins with high hardness, low brittleness and a low tendency to yellowing.

Another object of the invention is a curing agent suitable for curing epoxy resins, comprising the amine of formula (I) and at least one polyamine A, which has at least three epoxide group-reactive amine hydrogens.

Suitable polyamines A include in particular the following:

aliphatic, cycloaliphatic or arylaliphatic primary diamines, in particular 2,2-dimethyl-1,3-propanediamine, 1,3-pentanediamine (DAMP), 1,5-pentanediamine, 1,5-diamino-2-methylpentane (MPMD), 2-butyl-2-ethyl-1,5-pentanediamine (C11-neodiamine), 1,6-hexanediamine, 2,5-dimethyl-1,6-hexanediamine, 2,2,4- and 2,4,4-trimethylhexamethylenediamine (TMD), 1,7-heptanediamine, 1,8-octanediamine, 1,9-nonanediamine, 1,10-decanediamine, 1,11-undecanediamine, 1,12-dodecanediamine, 1,2-, 1,3- and 1,4-diaminocyclohexane, bis-(4-aminocyclohexyl)-methane ($H_{12}$-MDI), bis-(4-amino-3-methylcyclohexyl)-methane, bis-(4-amino-3-ethylcyclohexyl)-methane, bis-(4-amino-3,5-dimethylcyclohexyl)-methane, bis-(4-amino-3-ethyl-5-methylcyclohexyl)-methane, 1-amino-3-aminomethyl-3,5,5-trimethylcyclohexane (=isophoronediamine or IPDA), 2- and 4-methyl-1,3-diaminocyclohexane and mixtures thereof, 1,3- and 1,4-bis-(aminomethyl)-cyclohexane, 2,5(2,6)-bis-(aminomethyl)-bicyclo[2.2.1]heptane (NBDA), 3(4),8(9)-bis-(aminomethyl)-tricyclo[5.2.1.0$^{2,6}$]-decane, 1,4-diamino-2,2,6-trimethylcyclohexane (TMCDA), 1,8-menthanediamine, 3,9-bis-(3-aminopropyl)-2,4,8,10-tetraoxaspiro[5.5]undecane as well as 1,3- and 1,4-bis-(aminomethyl)-benzene;

aliphatic, cycloaliphatic or arylaliphatic primary triamines, in particular 4-aminomethyl-1,8-octanediamine, 1,3,5-tris-(aminomethyl)-benzene, 1,3,5-tris-(aminomethyl)-cyclohexane, tris-(2-aminoethyl)-amine, tris-(2-aminopropyl)-amine and tris-(3-aminopropyl)-amine;

ether group-containing aliphatic primary diamines, in particular bis-(2-aminoethyl)-ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine and higher oligomers of these diamines, bis-(3-aminopropyl)-polytetrahydrofurans and other polytetrahydrofuran diamines, cycloaliphatic ether group-containing diamines from the propoxylation and subsequent amination of 1,4-dimethylolcyclohexane, available in particular as Jeffamine® RFD-270 (from Huntsman), as well as polyoxyalkylene diamines which are typically products of the amination of polyoxyalkylene diols and are available, for example under the name Jeffamine® (Huntsman), under the name Polyetheramine (from BASF) or under the name PC Amine® (from Nitroil). Particularly suitable polyoxyalkylene diamines are Jeffamine® D-230, Jeffamine® D-400, Jeffamine® D-2000, Jeffamine® EDR-104, Jeffamine® EDR-148 and Jeffamine® EDR-176, and corresponding amines from BASF or Nitroil;

primary polyoxyalkylene triamines, which typically represent products of the amination of polyoxyalkylene triols and are available under the name Jeffamine® (from Huntsman), under the name Polyetheramine (from BASF) or under the name PC Amine® (from Nitroil), in particular Jeffamine® T-403, Jeffamine® T-3000, Jeffamine® T-5000, and corresponding amines from BASF or Nitroil;

tertiary amino group-containing polyamines having two primary aliphatic amino groups, such as in particular N,N'-bis-(aminopropyl)-piperazine, N,N-bis-(3-aminopropyl)-methylamine, N,N-bis-(3-aminopropyl)-ethylamine, N,N-bis-(3-aminopropyl)-propylamine, N,N-bis-(3-aminopropyl)-cyclohexylamine, N,N-bis-(3- aminopropyl)-2-ethylhexylamine, as well as the products of the double cyanoethylation and subsequent reduction of fatty amines, which are derived from natural fatty acids, such as N,N-bis-(3-aminopropyl)-dodecylamine and N,N-bis-(3-aminopropyl)-tallow-alkylamine, available as Triameen® Y12D and Triameen® YT (from Akzo Nobel);

tertiary amino group-containing polyamines with three primary aliphatic amino groups, such as in particular tris-(2-aminoethyl)-amine, tris-(2-aminopropyl)-amine, and tris-(3-aminopropyl)-amine;

secondary amino group-containing polyamines having two primary aliphatic amino groups, such as in particular 3-(2-aminoethyl)-aminopropylamine, bis-(hexamethylene)-triamine (BHMT), diethylenetriamine (DETA), triethylenetetramine (TETA), tetraethylenepentamine (TEPA), pentaethylenehexamine (PEHA) and higher homologs of linear polyethylene amines such as polyethylenepolyamine having 5 to 7 ethylene amine units (so-called "higher ethylenepolyamine", HEPA), products of multiple cyanoethylations or cyanobutylations and subsequent hydrogenation of primary di- and polyamines having at least two primary amino groups such as dipropylenetriamine (DPTA), N-(2-aminoethyl)-1,3-propanediamine (N3-Amine), N,N'-bis-(3-aminopropyl)-ethylendiamine (N4-Amine), N,N'-bis-(3-aminopropyl)-1,4-diaminobutane, N5-(3-aminopropyl)-2-methyl-1,5-pentanediamine, N3-(3-aminopentyl)-1,3-pentanediamine, N5-(3-amino-1-ethylpropyl)-2-methyl-1,5-pentanediamine and N,N'-bis-(3-amino-1-ethylpropyl)-2-methyl-1,5-pentanediamine;

one primary and one secondary amino group-containing polyamines, such as in particular N-butyl-1,2-ethanediamine, N-hexyl-1,2-ethanediamine, N-(2-ethylhexyl)-1,2-ethanediamine, N-cyclohexyl-1,2-ethanediamine, 4-aminomethylpiperidine, N-(2-aminoethyl)-piperazine, N-methyl-1,3-propanediamine, N-butyl-1,3-propanediamine, N-(2-ethylhexyl)-1,3-propanediamine, N-cyclohexyl-1,3-propanediamine, 3-methylamino-1-pentylamine, 3-ethylamino-1-pentylamine, 3-cyclohexylamino-1-pentylamine, fatty diamines such as N-cocoalkyl-1,3-propanediamine and products of the Michael-type addition reaction of primary aliphatic diamines with acrylonitrile, maleic or fumaric diesters, citraconic diesters, acrylic and methacrylic esters, acrylic and methacrylic amides and itaconic diesters, reacted in the molar ratio of 1:1, furthermore products of the partial reductive alkylation of primary aliphatic polyamines with aldehydes or ketones, in particular N-2-ethylhexyl-1,3-bis-(aminomethyl)-benzene, as well as partially styrenated polyamines such as Gaskamine® 240 (from Mitsubishi Gas Chemical (MGC));

aromatic polyamines such as in particular m- and p-phenylenediamine, 4,4'-, 2,4' and 2,2'-diaminodiphenylmethane, 3,3'-dichloro-4,4'-diaminodiphenylmethane (MOCA), 2,4- and 2,6-toluenediamine, mixtures of 3,5-dimethylthio-2,4- and 2,6-toluylenediamine (available as Ethacure® 300 from Albemarle), mixtures of 3,5-diethyl-2,4- and -2,6-toluylenediamine (DETDA), 3,3',5,5'-tetraethyl-4,4'-diaminodiphenylmethane (M-DEA), 3,3',5,5'-tetraethyl-2,2'-dichloro-4,4'-diaminodiphenylmethane (M-CDEA), 3,3'-diisopropyl-5,5'-dimethyl-4,4'-diaminodiphenylmethane (M-MIPA), 3,3',5,5'-tetraisopropyl-4,4'-diaminodiphenylmethane (M-DIPA), 4,4'-diaminodiphenylsulfone (DDS), 4-amino-N-(4-aminophenyl)-benzenesulfonamide, 5,5'-methylenedianthranilic acid, dimethyl-(5,5'-methylenedianthranilate), 1,3-propylene-bis-(4-aminobenzoate), 1,4-butylene-bis-(4-aminobenzoate), polytetramethyleneoxide-bis-(4-aminobenzoate) (available as Versalink® from Air Products), 1,2-bis-(2-aminophenylthio)-ethane, 2-methylpropyl-(4-chloro-3,5-diaminobenzoate) and tert-butyl-(4-chloro-3,5-diaminobenzoate);

adducts of these polyamines with epoxides and epoxy resins, in particular adducts with diepoxides in a molar ratio of about 2/1, adducts with monoepoxides in a molar ratio of at least 1/1, and reaction products of amines and epichlorohydrin, in particular that of 1,3-bis-(aminomethyl)-benzene, commercially available as Gaskamine® 328 (from MGC);

polyamidoamines, which are reaction products of a mono- or polyvalent carboxylic acid, or their esters or anhydrides, in particular a dimer fatty acid and an aliphatic, cycloaliphatic or aromatic polyamine that is used in stoichiometric excess, in particular a polyalkyleneamine such as DETA or TETA, in particular the commercially available polyamidoamines Versamid® 100, 125, 140 and 150 (from Cognis), Aradur® 223, 250 and 848 (from Huntsman), Euretek® 3607 and 530 (from Huntsman) and Beckopox® EH 651, EH 654, EH 655, EH 661 and EH 663 (from Cytec); and phenalkamines, also called Mannich bases, which are reaction products of a Mannich reaction of phenols, in particular cardanol, with aldehydes, in particular formaldehyde, and polyamines, in particular the commercially available phenalkamines Cardolite® NC-541, NC-557, NC-558, NC-566, Lite 2001 and Lite 2002 (from Cardolite), Aradur® 3440, 3441, 3442 and 3460 (from Huntsman) and Beckopox® EH 614, EH 621, EH 624, EH 628 and EH 629 (from Cytec).

Preferably, the polyamine A is selected from the group consisting of 1,5-diamino-2-methylpentane (MPMD), 2-butyl-2-ethyl-1,5-pentanediamine (C11-neodiamine), 1,6-hexanediamine, 2,2,4- and 2,4,4-trimethylhexamethylenediamine (TMD), 1,12-dodecanediamine, 1,3-diaminocyclohexane, bis-(4-aminocyclohexyl)-methane (HMDA), bis-(4-amino-3-methylcyclohexyl)-methane, 1-amino-3-aminomethyl-3,5,5-trimethylcyclohexane (IPD), 1,3-bis-(aminomethyl)-cyclohexane, 1,3-bis-(aminomethyl)-benzene (MXDA), bishexamethylenetriamine (BHMT), diethylenetriamine (DETA), triethylenetetramine (TETA), tetraethylenepentamine (TEPA), pentaethylenehexamine (PEHA) and higher homologs of linear polyethyleneamines such as polyethylenepolyamine having 5 to 7 ethylene amine units (HEPA), dipropylenetriamine (DPTA), N-(2-aminoethyl)-1,3-propanediamine (N3-Amine), N,N'-bis-(3-aminopropyl)-ethylendiamine (N4-Amine), cycloaliphatic ether group-containing diamines from the propoxylation and subsequent amination of 1,4-dimethylolcyclohexane having a molecular weight ranging from 200 to 300 g/mol, in particular Jeffamine® RFD-270 (from Huntsman), polyoxyalkylenediamines and polyoxyalkylenetriamines having a molecular weight ranging from 200 to 500 g/mol, in particular the types Jeffamine® D-230, Jeffamine® D-400 and Jeffamine® T-403, as well as derivatives of these polyamines in the form of adducts with epoxides, in particular monoepoxides or epoxy resins, or in the form of Michael adducts, Mannich bases or polyamido amines.

These preferred polyamines A are particularly compatible with epoxy resins and enable high quality films.

Particularly preferably, the polyamine A is an adduct with an epoxide, in particular an adduct with an epoxy resin or a monoepoxide. Such adducts exhibit excellent properties as curing agents for epoxy resins, in particular a fast cure rate, even at low temperatures, and a low tendency to blushing effects. They produce films of excellent quality, but due to their high viscosity, they are only suitable for coating applications if they are strongly diluted. In the prior art, this is typically accomplished by mixtures containing non-incorporable diluents and larger quantities of small, relatively volatile primary diamines. However, if the intention is not to use non-incorporable diluents, such curing agents are either too highly viscous or lead to severe blushing effects. By diluting such adducts with the amine of formula (I), curing agents for epoxy resins are available having excellent properties for low-emission coatings.

Particularly preferably, the polyamine A is an adduct with an aromatic monoepoxide. Such adducts have a moderate viscosity and exhibit good compatibility with epoxy resins.

Particularly preferred monoepoxides are aromatic glycidyl ethers, in particular the cresyl glycidyl ethers. Suitable cresyl glycidyl ethers include all isomeric cresyl glycidyl ethers and mixtures thereof, in particular commercially available types such as Araldite® DY-K (from Huntsman), Polypox™ R6 (from Dow), Heloxy™ KR (from Hexion) or Erisys® GE-10 (from CVC Spec. Chem.). Such adducts exhibit particularly good compatibility with the common epoxy resin products and enable cured films of high gloss and high hardness.

In an aspect of the invention, the curing agent contains at least two different polyamines A, in particular at least one polyamine A1, which preferably is an adduct with an epoxide, and at least one polyamine A2, which is a polyamine not having formed an adduct. Diluting such a mixture of polyamine A1 and polyamine A2 with the amine of formula (I) makes it possible to keep both the viscosity and the content of primary amino groups low enough so that low-emission coatings with good processability, low tendency to blushing effects, fast curing and low brittleness can be obtained.

Preferably, the amine of formula (I) is present in the curing agent in an amount such that its amine hydrogens constitute 1 to 75%, preferably 2 to 50%, in particular 5 to 30%, of all amine hydrogens present in the curing agent.

Further preferably, the amine of formula (I) is present in the curing agent in an amount such that the weight proportion constitutes 1 to 95%, preferably 5 to 75%, in particular 5 to 50% of the sum of all epoxide group-reactive amines.

Such curing agents are characterized by low viscosity and enable epoxy resin coatings with a high cure rate, hardly any tendency to blushing effects and high hardness with low brittleness.

The curing agent may further contain at least one accelerator. Suitable accelerators are substances which accelerate the reaction between amino groups and epoxy groups, in particular acids or compounds that are hydrolysable with formation of acids, in particular organic carboxylic acids such as acetic acid, benzoic acid, salicylic acid, 2-nitrobenzoic acid, lactic acid, organic sulfonic acids such as methanesulfonic acid, p-toluenesulfonic acid or 4-dodecylbenzene sulfonic acid, sulfonic acid esters, other organic or inorganic acids such as, in particular, phosphoric acid, or mixtures of the aforementioned acids and acid esters; furthermore tertiary amines such as in particular 1,4-diazabicyclo[2.2.2]octane, benzyldimethylamine, α-methylbenzyldimethylamine, triethanolamine, dimethylaminopropylamine, imidazoles such as in particular N-methylimidazole, N-vinylimidazole or 1,2-dimethylimidazole, salts of such tertiary amines, quaternary ammonium salts, such as in particular benzyltrimethylammonium chloride, amidines such as in particular 1,8-diazabicyclo[5.4.0]undec-7-ene, guanidines such as in particular 1,1,3,3-tetramethylguanidine, phenols, in particular bisphenols, phenolic resins, and Mannich bases, such as in particular 2-(dimethylaminomethyl)-phenol, 2,4,6-tris-(dimethylaminomethyl)-phenol, and polymers made of phenol, formaldehyde and N,N-dimethyl-1,3-propanediamine, phosphites such as in particular di- and triphenylphosphites, and mercapto group-containing compounds.

Preferred accelerators are salicylic acid and 2,4,6-tris-(dimethylaminomethyl)-phenol.

The curing agent may further contain at least one non-incorporable diluent, in particular xylene, 2-methoxyethanol, dimethoxyethanol, 2-ethoxyethanol, 2-propoxyethanol, 2-isopropoxyethanol, 2-butoxyethanol, 2-phenoxyethanol, 2-benzyloxyethanol, benzyl alcohol, ethylene glycol, ethylene glycol dimethyl ether, ethylene glycol diethyl ether, ethylene glycol dibutyl ether, ethylene glycol diphenyl ether, diethylene glycol, diethylene glycol monomethyl ether, diethylene glycol monoethyl ether, diethylene glycol mono-n-butyl ether, diethylene glycol dimethyl ether, diethylene glycol diethyl ether, diethylene glycol di-n-butylylether, propylene glycol butyl ether, propylene glycol phenyl ether, dipropylene glycol, dipropylene glycol monomethyl ether, dipropylene glycol dimethyl ether, dipropylene glycol di-n-butyl ether, N-methylpyrrolidone, diphenylmethane, diisopropylnaphthalene, petroleum fractions such as Solvesso® types (from Exxon), alkylphenols such as tert-butylphenol, nonylphenol, dodecylphenol and 8,11,14-pentadecatrienylphenol (cardanol from cashew nut shell oil, available, for example, as Cardolite NC-700 from Cardolite Corp., USA), styrenated phenol, bisphenols, aromatic hydrocarbon resins, in particular phenol group-containing types, alkoxylated phenol, in particular ethoxylated or propoxylated phenol, in particular 2-phenoxyethanol, adipates, sebacates, phthalates, benzoates, organic phosphates and sulfonates and sulfonamides. Benzyl alcohol, dodecyl phenol, tert-butylphenol, styrenated phenol, ethoxylated phenol and phenol group-containing aromatic hydrocarbon resins, in particular the Novares® types LS 500, LX 200, LA 300 and LA 700 (from Rütgers) are preferred.

Preferably, the curing agent contains no or only a low content of non-incorporable diluents, particularly preferably less than 25% by weight, in particular less than 10% by weight and most preferably less than 5% by weight. In particular, no non-incorporable diluents are added to the curing agent.

The curing agent may contain additional epoxide group-reactive substances, for example monoamines, such as hexylamine and benzylamine; secondary aliphatic polyamines; mercapto group-containing compounds, in particular the following:
  liquid mercaptan-terminated polysulfide polymers, known under the brand name Thiokol® (from Morton Thiokol; for example, available from SPI Supplies, or from Toray Fine Chemicals), in particular the types LP-3, LP-33, LP-980, LP-23, LP-55, LP-56, LP-12, LP-31, LP-32, and LP-2; and also known under the brand name Thioplast® (from Akzo Nobel), in particular the types G 10, G 112, G 131, G 1, G 12, G 21, G 22, G 44, and G 4;
  mercaptan-terminated polyoxyalkylene ethers, obtainable for example by reaction of polyoxyalkylene diols and triols either with epichlorohydrin or with an alkylene oxide, followed by sodium hydrogen sulfide;

mercaptan-terminated compounds in the form of polyoxyalkylene derivatives, known under the brand name Capcure®(from Cognis), in particular the types WR-8, LOF and 3-800;

polyesters of thiocarboxylic acids, for example pentaerythritol tetramercaptoacetate, trimethylolpropane trimercaptoacetate, glycol dimercaptoacetate, pentaerythritol tetra-(3-mercaptopropionate), trimethylolpropane tri-(3-mercaptopropionate) and glycol di-(3-mercaptopropionate) and the esterification products of polyoxyalkylene diols and triols, ethoxylated trimethylolpropane and polyester diols with thiocarboxylic acids such as thioglycolic acid and 2- or 3-mercaptopropionic acid; and other mercapto group-containing compounds such as in particular 2,4,6-trimercapto-1,3,5-triazine, 2,2'-(ethylenedioxy)-diethanethiol (triethylene glycol dimercaptan) and ethanedithiol.

Another object of the invention is an epoxy resin composition containing at least one epoxy resin and the curing agents described above.

Suitable epoxy resins include common technical epoxy resins. These are obtained in a known manner, for example from the oxidation of the appropriate olefins, or from the reaction of epichlorohydrin with the appropriate polyols, polyphenols or amines.

Particularly suitable epoxy resins include so-called polyepoxide liquid resins, hereinafter referred to as "liquid resin". These have a glass transition temperature below 25° C.

Other suitable epoxy resins include so-called solid resins which have a glass transition temperature above 25° C. and can be comminuted to powders that are free-flowing at 25° C.

Suitable epoxy resins are in particular aromatic epoxy resins, in particular the glycidylization products of:

Bisphenol A, Bisphenol F or Bisphenol A/F, where A represents acetone and F represents formaldehyde, which served as starting materials for the preparation of these bisphenols. In the case of Bisphenol F, positional isomers can be present as well, in particular derived from 2,4'- and 2,2'-hydroxyphenylmethane;

dihydroxybenzene derivatives, such as resorcinol, hydroquinone and pyrocatechol;

other bisphenols or polyphenols, such as bis-(4-hydroxy-3-methylphenyl)-methane, 2,2-bis-(4-hydroxy-3-methylphenyl)-propane (Bisphenol C), bis-(3,5-dimethyl-4-hydroxyphenyl)-methane, 2,2-bis-(3,5-dimethyl-4-hydroxyphenyl)-propane, 2,2-bis-(3,5-dibromo-4-hydroxyphenyl)-propane, 2,2-bis-(4-hydroxy-3-tert-butylphenyl)-propane, 2,2-bis-(4-hydroxyphenyl)-butane (Bisphenol B), 3,3-bis-(4-hydroxyphenyl)-pentane, 3,4-bis-(4-hydroxyphenyl)-hexane, 4,4-bis-(4-hydroxyphenyl)-heptane, 2,4-bis-(4-hydroxyphenyl)-2-methylbutane, 2,4-bis-(3,5-dimethyl-4-hydroxyphenyl)-2-methylbutane, 1,1-bis-(4-hydroxyphenyl)-cyclohexane (Bisphenol Z), 1,1-bis-(4-hydroxyphenyl)-3,3,5-trimethylcyclohexane (Bisphenol TMC), 1,1-bis-(4-hydroxyphenyl)-phenylethane, 1,4-bis-[2-(4-hydroxyphenyl)-2-propyl]-benzene (Bisphenol P), 1,3-bis-[2-(4-hydroxyphenyl)-2-propyl]-benzene (Bisphenol M), 4,4'-dihydroxydiphenyl (DOD), 4,4'-dihydroxybenzophenone, bis-(2-hydroxynaphth-1-yl)-methane, bis-(4-hydroxynaphth-1-yl)-methane, 1,5-dihydroxynaphthalene, tris-(4-hydroxyphenyl)-methane, 1,1,2,2-tetrakis-(4-hydroxyphenyl)-ethane, bis-(4-hydroxyphenyl)-ether and bis-(4-hydroxyphenyl)-sulfone;

condensation products of phenols with formaldehyde which are obtained under acid condition, such as phenol novolacs or cresol novolacs, also known as Bisphenol F novolacs;

aromatic amines such as aniline, toluidine, 4-aminophenol, 4,4'-methylenediphenyldiamine, 4,4'-methylenediphenyldi-(N-methyl)-amine, 4,4'-[1,4-phenylene-bis-(1-methylethylidene)]-bisaniline (Bisaniline P), 4,4'-[1,3-phenylene-bis-(1-methylethylidene)]-bisaniline (Bisaniline M).

Other suitable epoxy resins include aliphatic or cycloaliphatic polyepoxides, in particular glycidyl ethers of saturated or unsaturated, branched or unbranched, cyclic or open-chain di-, tri- or tetrafunctional $C_2$ to $C_{30}$ alcohols, in particular ethylene glycol, propylene glycol, butylene glycol, hexanediol, octanediol, polypropylene glycols, dimethylolcyclohexane, neopentylglycol, dibromo-neopentyl glycol, castor oil, trimethylolpropane, trimethylolethane, pentaerythritol, sorbitol or glycerol, as well as alkoxylated glycerol or alkoxylated trimethylolpropane;

a hydrogenated Bisphenol A, F or A/F liquid resin, or the glycidylization products of hydrogenated Bisphenol A, F, or A/F;

a N-glycidyl derivative of amides or heterocyclic nitrogen bases, such as triglycidyl cyanurate and triglycidyl isocyanurate, as well as reaction products of epichlorohydrin and hydantoin.

epoxy resins from the oxidation of olefins, such as in particular vinylcyclohexene, dicyclopentadiene, cyclohexadiene, cyclododecadiene, cyclododecatriene, isoprene, 1,5-hexadiene, butadiene, polybutadiene, or divinylbenzene.

Preferably, the epoxy resin is a liquid resin based on a bisphenol, in particular a diglycidyl ether of Bisphenol A, Bisphenol F or Bisphenol A/F, commercially available, for example, from Dow, Huntsman, and Hexion. As epoxy resins, these liquid resins have a low viscosity and in the cured state exhibit good properties as a coating. Optionally they may be present in combination with Bisphenol A solid resin or Bisphenol F novolac epoxy resin.

The epoxy resin may contain a reactive diluent, in particular a reactive diluent having at least one epoxide group. Suitable reactive diluents include, for example, the glycidyl ethers of mono- or polyhydric phenols and aliphatic or cycloaliphatic alcohols, such as in particular polyglycidyl ethers of diols or polyols already mentioned above, and furthermore in particular phenyl glycidyl ether, cresyl glycidyl ether, benzyl glycidyl ether, p-n-butyl-phenyl glycidyl ether, p-tert-butyl-phenyl glycidyl ether, nonyl phenyl glycidyl ether, allyl glycidyl ether, butyl glycidyl ether, hexyl glycidyl ether, 2-ethylhexyl glycidyl ether, as well as glycidyl ethers of natural alcohols, such as, for example, $C_8$ to $C_{10}$ alkyl glycidyl ethers, or $C_{12}$ to $C_{14}$ alkyl glycidyl ethers. The addition of a reactive diluent to the epoxy resin effects a reduction in viscosity as well as a reduction in glass transition temperature and mechanical parameters.

Optionally, the epoxy resin composition contains other components, in particular auxiliaries and additives commonly used in epoxy resin compositions, for example the following:

solvents, diluents, film-forming agents or extenders, such as in particular the non-incorporable diluents already mentioned above;

reactive diluents, in particular reactive diluents having epoxide groups, such as those mentioned above, epoxidized soybean oil or linseed oil, compounds having acetoacetate groups, in particular acetoacetylated polyols, butyrolactone, carbonates, aldehydes, isocyanates, and furthermore isocyanates and silicones having reactive groups;

polymers, in particular polyamides, polysulfides, polyvinyl formal (PVF), polyvinyl butyral (PVB), polyurethanes (PUR), polymers having carboxyl groups, polyamides, butadiene-acrylonitrile copolymers, styrene-acrylonitrile copolymers, butadiene-styrene copolymers, homo- or copolymers of unsaturated monomers, in particular from the group comprising ethylene, propylene, butylene, isobutylene, isoprene, vinyl acetate and alkyl-(meth)acrylates, in particular chlorosulfonated polyethylenes and fluorine-containing polymers, sulfonamide-modified melamines and purified montan waxes;

inorganic and organic fillers, for example, ground or precipitated calcium carbonates, which are optionally coated with fatty acids, in particular stearates, barite (heavy spar), talcs, powdered quartz, silica sand, iron mica, dolomite, wollastonite, kaolin, mica (potassium aluminum silicate), molecular sieves, aluminum oxides, aluminum hydroxides, magnesium hydroxide, silicas, cements, gypsums, fly ashes, carbon black, graphite, metal powders such as aluminum, copper, iron, zinc, silver or steel, PVC powder or hollow spheres;

fibers, in particular glass fibers, carbon fibers, metal fibers, ceramic fibers or plastic fibers such as polyamide fibers or polyethylene fibers;

pigments, in particular titanium dioxide and iron oxides;

the accelerators mentioned above;

rheology modifiers, in particular, thickeners or anti-settling agents;

adhesion promoters, in particular organoalkoxysilanes;

stabilizers against oxidation, heat, light and UV radiation;

flame-retardant substances, in particular aluminum hydroxide (ATH), magnesium dihydroxide (MDH), antimony trioxide, antimony pentoxide, boric acid $(B(OH)_3)$, zinc borate, zinc phosphate, melamine borate, melamine cyanurate, ammonium polyphosphate, melamine phosphate, melamine pyrophosphate, polybrominated diphenyl oxides or diphenyl ethers, phosphates, such as in particular diphenyl cresyl phosphate, resorcinol-bis-(diphenylphosphate), resorcinol-diphosphate-oligomers, tetraphenylresorcinol diphosphite, ethylenediamine diphosphate and Bisphenol A-bis-(diphenylphosphate), tris-(chloroethyl)-phosphate, tris-(chloropropyl)-phosphate and tris-(dichloroisopropyl)-phosphate, tris-[3-bromo-2,2-bis-(bromomethyl)-propyl]-phosphate, tetrabromo-Bisphenol A, bis-(2,3-dibromopropylether) of Bisphenol A, brominated epoxy resins, ethylene-bis-(tetrabromophthalimide), ethylene-bis-(dibromonorbornanedicarboximide), 1,2-bis-(tribromophenoxy)-ethane, tris-(2,3-dibromopropyl)-isocyanurate, tribromophenol, hexabromocyclododecane, bis-(hexachlorocyclopentadieno)-cyclooctane and chloroparaffins;

surface-active substances, in particular wetting agents, leveling agents, deaerating agents, and defoamers;

biocides, such as algicides, fungicides or fungal growth inhibiting substances.

Preferably, the epoxy resin composition further contains other auxiliaries and additives, in particular wetting agents, leveling agents, defoamers, stabilizers, pigments and catalysts, in particular salicylic acid or 2,4,6-tris-(dimethylaminomethyl)-phenol.

Preferably, the epoxy resin composition contains no or only a low content of non-incorporable diluents, particularly preferably less than 10% by weight, in particular less than 5% by weight, most preferably less than 2% by weight.

In the epoxy resin composition, the ratio of the number of epoxide group-reactive groups to the number of epoxide groups preferably ranges from 0.5 to 1.5, in particular 0.7 to 1.2. The amine hydrogens present in the epoxy resin composition and any optionally present additional epoxide group-reactive groups react with the epoxide groups under ring opening thereof (addition reaction). As a result of these reactions the composition polymerizes and ultimately cures. The skilled person knows that primary amino groups are difunctional with respect to epoxide groups and one primary amino group thus counts as two epoxide group-reactive groups.

In particular, the epoxy resin composition is a two-component composition, consisting of (i) a resin component containing at least one epoxy resin, and (ii) a curing agent component containing the curing agent described above.

The components of the two-component composition are each stored in a separate container. Other components of the two-component epoxy resin composition can be present as part of the resin or the curing agent component, wherein other epoxide group-reactive components are preferably constituents of the curing agent component. A suitable container for storing the resin or curing agent component is in particular a barrel, a hobbock, a bag, a bucket, a can, a cartridge or a tube. The components can be stored, which means that before they are used they can be stored for several months to a year or more without their properties changing to an extent that is relevant to their use. When applying the two-component epoxy resin composition, the resin and the curing agent component are mixed together just before or during application. The mixing ratio between the two components is preferably chosen such that the epoxide group-reactive groups of the curing agent component are in an appropriate ratio to the epoxide groups of the resin component, as described above. In parts by weight, the mixing ratio between the resin component and the curing agent component usually ranges from 1:10 to 10:1. The mixing of the two components is carried out by a suitable method; it may be continuous or batchwise. If the mixing is carried out prior to application, care must be taken that not too much time passes between the mixing of the components and the application, as this may lead to failures, such as, for example, slow or incomplete development of adhesion to the substrate. The mixing takes place in particular at ambient temperature, which typically ranges from about 5 to 50° C., preferably from about 10 to 30° C.

Upon mixing of the two components, the curing begins by chemical reaction, as described above. Curing takes place in particular at ambient temperature. Typically, it extends over several days or weeks until it is largely completed under the given conditions. The time depends, inter alia, on the temperature, the reactivity of the components and their stoichiometry, and the presence of accelerators.

Another object of the invention is thus also a cured composition obtained from the curing of an epoxy resin composition as described in the present document.

The epoxy resin composition is applied to at least one substrate, the following being particularly suitable:
- glass, glass ceramic, concrete, mortar, brick, tile, gypsum and natural stones such as granite or marble;
- metals and alloys, such as aluminum, iron, steel and nonferrous metals, including surface-coated metals and alloys such as zinc and chrome-plated metals;
- leather, textiles, paper, wood, wood materials bonded with resins, for example, phenolic, melamine or epoxy resins, resin-textile composites and other so-called polymer composites;
- plastics, in particular hard and soft PVC, ABS, polycarbonate (PC), polyamide (PA), polyester, PMMA, epoxy resins, PUR, POM, PO, PE, PP, EPM and EPDM, wherein the plastics are optionally surface-treated by plasma, corona or flames;
- fiber-reinforced plastics such as carbon fiber-reinforced plastics (CFRP), glass fiber-reinforced plastics (GRP) and sheet molding compounds (SMC);
- coated substrates such as powder-coated metals or alloys;
- paints and varnishes.

The substrates may be pretreated prior to application of the epoxy resin composition, if necessary. Such pretreatments include in particular physical and/or chemical cleaning methods, for example, grinding, sand blasting, shot blasting, brushing and/or blowing, and furthermore treating with cleaning agents or solvents, or the application of an adhesion promoter, an adhesion promoter solution or a primer.

The epoxy resin composition described can be used advantageously as a fiber composite material (composite), grouting, sealant, adhesive, coating, plating, painting, paint, sealer, undercoat or primer. In particular, it can be used as a grouting, sealant and adhesive, such as, for example, as a potting compound, sealant, vehicle body adhesive, sandwich panel adhesive, half-shell adhesive, for example for rotor blades of wind power plants, bridge element adhesive, or anchoring adhesive; and furthermore as covering, coating, paint, varnish, sealer, undercoat and primer for construction and industrial applications, such as, in particular, as floor covering and floor coating for interiors such as offices, industrial halls, gymnasiums or cold rooms, or outdoors for balconies, terraces, parking decks, bridges or roofs, as a protective coating for concrete, cement, metals, plastics or wood, for example for surface sealing of wooden structures, vehicles, loading platforms, tanks, silos, wells, ducts, pipelines, machinery or steel structures, for example, of ships, piers, offshore platforms, lock gates, hydroelectric plants, river works, swimming pools, wind power plants, bridges, chimneys, cranes or sheet pilings; and furthermore as prime coat, finishing, corrosion protection primer or for making surfaces hydrophobic. Another coating, another covering or another paint can be applied to the fully or partially cured epoxy resin composition, in particular, when used as a coating, covering or paint, wherein this further layer may likewise be an epoxy resin composition, but also another material, in particular a polyurethane or polyurea coating.

Particularly advantageously the epoxy resin composition described can be used as a coating. In this context, coatings mean flat covers of all kinds, in particular paints, varnishes, sealers, undercoats and primers, as described above.

Particularly advantageously the epoxy resin composition described can be used in low-emission epoxy resin products with eco-certification, for example according to Emicode (EC1 Plus), AgBB, DIBt, Der Blaue Engel, AFSSET, RTS (M1) and US Green Building Council (LEED).

The epoxy resin composition is advantageously used as a coating in a method of coating, wherein it has a liquid consistency with a low viscosity and good leveling properties and can be applied in particular as a self-leveling coating to predominantly flat surfaces or as a paint. Preferably, in this application the epoxy resin composition immediately after mixing of the resin and the curing agent component has a viscosity, measured at 20° C., ranging from 300 to 2,000 mPa·s, preferably ranging from 300 to 1,500 mPa·s, particularly preferably ranging from 300 to 1,200 mPa·s. Within the processing time, the mixed composition is applied flat as a thin film to a substrate with a layer thickness of typically about 50 μm to about 5 mm, typically at ambient temperature. The application is effected in particular by pouring onto the substrate to be coated and subsequent uniform distribution using, for example, a squeegee or a serrated trowel. The application can also be effected with a brush or roller or as a spray application, for example as corrosion protection coating on steel.

Upon curing, typically largely clear, glossy and non-sticky films of high hardness, low brittleness and a low tendency to yellowing form, which have good adhesion to various substrates. A film of high hardness and low brittleness preferably has a hardness according to König (pendulum hardness according to König, measured according to DIN EN ISO 1522) ranging from 100 to 200 s, in particular from 120 to 180 s. An even higher hardness according to König also typically has increased brittleness, and a lower hardness according to König is too soft for many coating applications.

Another object of the invention is an article containing a cured composition obtained by curing of the epoxy resin composition described above. The cured composition is present in particular in the form of a coating.

The epoxy resin composition described is characterized by advantageous properties. It has low viscosity and cures even under cold, damp conditions quickly and largely without blushing effects, thereby making available clear films of high hardness, low brittleness and low tendency to yellowing, even with small proportions or completely without the use of non-incorporable diluents and with small proportions or completely without the use of small, relatively volatile primary diamines. The epoxy resin composition described makes available low-emission epoxy resin products that meet the requirements for many eco-certifications and at the same time meet high standards in terms of safety, processing and use characteristics.

Examples

Exemplary embodiments are shown below, which are intended to illustrate the invention described in more detail. Of course, the invention is not limited to the exemplary embodiments described.

"AHEW" stands for the amine hydrogen equivalent weight.

"EEW" stands for the epoxide equivalent weight.

"MGC" stands for "Mitsubishi Gas Chemical".

"GT" stands for "parts by weight".

1. Description of the Measurement Methods

The amine content, that is, the total content of amino groups in the compounds prepared, was determined by titration (with 0.1 N $HClO_4$ in glacial acetic acid, vs. crystal violet) and is always reported in mmol N/g.

Infrared spectra (FT-IR) were measured as neat films with an FT-IR instrument 1600 from Perkin-Elmer equipped with a horizontal ATR measuring unit with ZnSe crystal; the absorption bands are reported in wavenumbers (cm$^{-1}$) (measurement window: 4000-650 cm$^{-1}$).

GC/MS was performed under the following conditions: column Agilent VF 5 ms, 30 m×0.25 mm, 0.25 μm film thickness; heating rate 15° C./min from 60° C. to 320° C., then held for 15 min at 320° C.; He carrier gas at a constant flow rate of 1.1 ml/min; injector split 25:1, temperature 230° C.; ionization method Cl$^+$ (methanol).

The viscosity was measured on a Rheotec RC30 cone-plate viscometer with thermostat (cone diameter 50 mm, cone angle 1°, cone tip-plate distance 0.05 mm, shear rate 10-100 s$^{-1}$).

2. Substances Used:

EP adduct 1: reaction product of 116.0 GT 1,5-diamino-2-methyl-pentane and 182 GT Araldite® DY-K; AHEW=99.4 g/eq; viscosity (20° C.)=5800 mPa·s EP adduct 2: reaction product of 136.2 GT 1,3-bis-(aminomethyl)-benzene and 182 GT Araldite® DY-K; AHEW=106.1 g/eq; viscosity (20° C.)=28,000 mPa·s Aradur® 3442 (Huntsman) Phenalkamin; AHEW=125 g/eq; viscosity (20° C.)=10,210 mPa·s Gaskamine® 240 (MGC) styrenized 1,3-bis-(aminomethyl)-benzene; AHEW=103 g/eq; viscosity (20° C.)=165 mPa·s Jeffamine® RFD-270 (Huntsman) cycloaliphatic ether group-containing diamine from the propoxylation and subsequent amination of 1,4-dimethylolcyclohexane; AHEW=67 g/eq Araldite® DY-K (Huntsman) monoglycidyl ether of cresol; EEW about 182 g/eq Araldite® GY 250 (Huntsman) Bisphenol A diglycidyl ether; EEW about 187.5 g/eq Araldite® DY-E (Huntsman) monoglycidyl ether of a $C_{12}$ to $C_{14}$ alcohol; EEW about 290 g/eq Ancamine® K 54 (Air Products) 2,4,6-tris-(dimethylaminomethyl)-phenol 3. Preparation of Amines Amine 1:
1,3-Bis-(2-ethylhexylaminomethyl)-benzene In a round bottom flask, 25.6 g (0.20 mol) of 2-ethylhexanal and 13.6 g (0.10 mol) of 1,3-bis-(aminomethyl)-benzene (from MGC) were dissolved in sufficient isopropanol under a nitrogen atmosphere. The solution was stirred for 30 minutes at room temperature and then hydrogenated at a hydrogen pressure of 80 bar, a temperature of 80° C. and a flow rate of 3 ml/min on a continuous hydrogenation apparatus with Pd/C fixed bed catalyst. To monitor the reaction, IR spectroscopy was used to check whether the imine band at about 1665 cm$^{-1}$ had disappeared. Then, the solution was concentrated in vacuo at 80° C. A clear, slightly yellowish liquid with a viscosity of 140 mPa·s at 20° C., an amine content of 5.50 mmol N/g, a purity of 87.7% (determined by gas chromatography) and a theoretical AHEW of about 180.3 g/eq was obtained.

FT-IR: 2956, 2923, 2857, 2811, 1457, 1378, 1156, 1113, 776, 726, 699.

GC/MS: $t_R$=15.56 min; m/z=361.0 ([MH$^+$]; theoretical mass for $C_{24}H_{44}N_2$: 360.35).

Amine 2: Reaction mixture containing 1,3-bis-(2-ethylhexylaminomethyl)-benzene and N-2-ethylhexyl-1,3-bis-(aminomethyl)-benzene In the same manner as described for Amine 1, 20.5 g (0.16 mol) of 2-ethylhexanal and 13.6 g (0.10 mol) of 1,3-bis-(aminomethyl)-benzene were reacted. A clear, slightly yellowish liquid with a viscosity of 100 mPa·s at 20° C., an amine content of 6.39 mmol N/g, a content of 1,3-bis-(2-ethylhexyl-aminomethyl)-benzene of 66.4% by weight, a content of N-2-ethylhexyl-1,3-bis-(aminomethyl)-benzene of 30.1% by weight (determined by gas chromatography) and a theoretical AHEW of about 130.2 g/eq was obtained.

Amine 3 (reference):
1,3-Bis-(benzylaminomethyl)-benzene

In the same manner as described for Amine 1, 21.2 g (0.20 mol) of benzaldehyde and 13.6 g (0.10 mol) of 1,3-bis-(aminomethyl)-benzene were reacted. A clear, slightly yellowish liquid with a viscosity of 230 mPa·s at 20° C., an amine content of 6.41 mmol N/g and a theoretical AHEW of about 158.2 g/eq was obtained.

Amine 4 (reference):
1,3-Bis-(2-methylpropylaminomethyl)-benzene

In the same manner as described for Amine 1, 14.4 g (0.2 mol) of isobutyraldehyde and 13.6 g (0.1 mol) of 1,3-bis-(aminomethyl)-benzene were reacted. A clear, slightly yellowish liquid with a viscosity of 100 mPa·s at 20° C., an amine content of 6.37 mmol N/g and a theoretical AHEW of about 124 g/eq was obtained.

Amine 5 (reference):
1,3-Bis-(n-octylaminomethyl)-benzene

In the same manner as described for Amine 1, 25.6 g (0.20 mol) of 1-octanal and 13.6 g (0.10 mol) of 1,3-bis-(aminomethyl)-benzene were reacted. A clear, slightly yellowish liquid with a viscosity of 130 mPa·s at 20° C., an amine content of 5.45 mmol N/g and a theoretical AHEW of about 180.3 g/eq was obtained.

Amine 6 (reference): N,N'-bis-(2-ethylhexyl)-1,5-diamino-2-methylpentane

In the same manner as described for Amine 1, 25.6 g (0.20 mol) of 1-octanal and 11.6 g (0.10 mol) of 1,5-diamino-2-methylpentane (Dytek® A from Invista) were reacted. A clear, slightly yellowish liquid with a viscosity of 140 mPa·s at 20° C., an amine content of 5.80 mmol N/g and a theoretical AHEW of about 170.3 g/eq was obtained.

4. Preparation of Curing Agents

For each example, the ingredients given in Table 1 in the specified amounts (parts by weight) were mixed by means of a centrifugal mixer (SpeedMixer™ DAC 150, FlackTek Inc.). The viscosity of the curing agent composition was determined 1 hour after mixing. The results are shown in Table 1.

HZ-1 to HZ-3 are curing agents according to the invention, Ref-1 to Ref-3 are comparison examples.

TABLE 1

Compositions, viscosities, and AHEW of the curing agents HZ-1 to HZ-3 and Ref-1 to Ref. 3

| Example | HZ-1 | HZ-2 | HZ-3 | Ref-1 | Ref-2 | Ref-3 |
| --- | --- | --- | --- | --- | --- | --- |
| EP adduct 1 | 74.6 | — | — | 74.6 | — | — |
| EP adduct 2 | — | 79.6 | — | — | 79.6 | — |
| Aradur ® 3442 | — | — | 93.8 | — | — | 93.8 |
| Amine 1 | 45.1 | 45.1 | 45.1 | — | — | — |

TABLE 1-continued

Compositions, viscosities, and AHEW of the curing agents HZ-1 to HZ-3 and Ref-1 to Ref. 3

| Example | HZ-1 | HZ-2 | HZ-3 | Ref-1 | Ref-2 | Ref-3 |
|---|---|---|---|---|---|---|
| Amine 3 | — | — | — | 39.6 | 39.6 | 39.6 |
| Viscosity [mPa·s] (20° C.) | 790 | 1240 | 1170 | 1650 | 2570 | 1730 |
| AHEW [g] | 119.6 | 126.9 | 138.8 | 114.2 | 121.5 | 133.4 |

Each curing agent of Table 1 contains Amine 1 or Amine 3 in an amount such that its amine hydrogens constitute 25% of all the amine hydrogens present in the curing agent.

5. Preparation of Curing Agents and Epoxy Resin Compositions

For each example, the ingredients given in Tables 2 to 3 in the specified amounts (parts by weight) of the curing agent component were mixed by means of a centrifugal mixer (SpeedMixer™ DAC 150, FlackTek Inc.) and stored under exclusion of moisture.

Likewise, the ingredients of the resin components given in Tables 2 to 3 were processed and stored.

Subsequently, the two components of each composition were processed to a homogeneous liquid by means of the centrifugal mixer and these were tested immediately as follows:

10 minutes after mixing, the viscosity at 20° C. was determined ("viscosity (10')").

A first film having a layer thickness of 500 μm was applied to a glass plate and stored at 23±1° C. and 50±5% relative humidity (=standard climate, hereinafter abbreviated as "NK"), or cured. The hardness according to König (pendulum hardness according to König, measured according to DIN EN ISO 1522) of this film was determined after 2 days ("hardness acc. to König (2d NK)") or after 4 days ("h. according to König (NK) (4d)") or after 7 days ("hardness according to König (7d NK)") or after 4 weeks ("hardness according to König (4w NK)"). After 4 weeks, the appearance of the film was evaluated (in the table referred to as "appearance (NK)"). Here, a film was called "nice", when it was clear and had a glossy and non-sticky surface without having structure. Here, "structure" refers to any kind of marking or pattern on the surface.

A second film having a layer thickness of 500 μm was applied to a glass plate and stored for 7 days at 8° C. and 80% relative humidity, and then for 3 weeks under NK, or cured. 24 hours after the application, a bottle cap made of polypropylene was placed on the film, and a damp sponge was placed under it. After another 24 hours, the sponge and the cap were removed and placed at a new location on the film, from which it was removed after 24 hours and placed again, a total of 4 times. Subsequently, the appearance of this film was evaluated (in the tables referred to as "appearance (8°/80%)"), in the same way as described for the appearance (NK). In each case, the number of markings which were visible on the film due to the damp sponge and/or the cap placed on the film was specified also. The presence of discoloration or clouding is also noted. The hardness according to König was also determined on films cured in this manner, in each case after 7 days at 8° C. and 80% relative humidity ("hardness according to König (7d cold)"), then after a further 2 days in NK ("hardness according to König (+2d NK)") or 7 days in NK ("hardness according to König (+7d NK)") or 3 weeks in NK ("hardness according to König (+3w NK)"). The yellowing was determined for film that was applied to a glass plate at a layer thickness of 500 μm and cured for 4 weeks in standard climate, and then was stored for 3 months on a sun-drenched terrace. The extent of the yellowing was evaluated visually in comparison to an area of the film covered with aluminum foil.

The results are shown in Tables 2 to 3.

EZ-1 to EZ-4 are examples according to the invention, and Ref-4 to Ref-11 are comparison examples.

TABLE 2

Composition and properties of EZ-1, EZ-2 and Ref-4 to Ref-8.

| | Ref-4 | EZ-1 | EZ-2 | Ref-5 | Ref-6 | Ref-7 | Ref-8 |
|---|---|---|---|---|---|---|---|
| Resin comp.: | | | | | | | |
| Araldite® GY-250 | 167.2 | 167.2 | 167.2 | 167.2 | 167.2 | 167.2 | 167.2 |
| Araldite® DY-E | 31.8 | 31.8 | 31.8 | 31.8 | 31.8 | 31.8 | 31.8 |
| Curing agent comp.: | | | | | | | |
| EP adduct 1 | 99.4 | 74.6 | 74.6 | 74.6 | 74.6 | 74.6 | 74.6 |
| Amine | — | -1 | -2 | -3 | -4 | -5 | 240 [1] |
| | | 45.1 | 32.6 | 39.6 | 31.1 | 45.1 | 25.8 |
| Ancamine® K54 | 6.0 | 6.4 | 6.2 | 6.3 | 6.2 | 6.4 | 6.0 |
| Viscosity (10') [Pa·s] | 2.90 | 1.11 | 1.45 | 1.54 | 1.65 | 1.10 | 1.62 |
| Hardness (2 d NK) | 145 | 77 | 131 | 133 | 104 | 78 | 116 |
| acc. to (4 d NK) | 176 | 88 | 141 | 170 | 123 | 84 | 160 |
| König [s] (7 d NK) | 196 | 88 | 142 | 172 | 130 | 87 | 176 |
| (4 w NK) | 198 | 106 | 147 | 200 | 147 | 90 | 193 |
| Appearance (NK) | nice | nice | nice | nice | turbid | l. turbid | turbid |
| Hardness (7 d cold) | 187 | 39 | 59 | 70 | 42 | 34 | 42 |
| acc. to (+2 d NK) | 161 | 75 | 125 | 147 | 87 | 67 | 66 |
| König (+7 d NK) | 185 | 97 | 140 | 165 | 120 | 80 | 133 |
| (8°/80%) [s] (+3 w NK) | 197 | 105 | 144 | 183 | 137 | 83 | 186 |
| Appearance (8°/80%) | l. matt | nice | l. matt | nice | turbid, coating | l. matt | nice |
| Number of markings | 4 (w) | none | none | none | none | 1 (w) | 4 (w) |
| Yellowing | minim | minim | minim | signif. | minim | minim | signif. |

"l" stands for "slightly";
"w" stands for "weak"
[1] Gaskamine® 240

TABLE 3

Composition and properties of EZ-3, EZ-4 and Ref-9 to Ref-11.

| | Example | | | | |
|---|---|---|---|---|---|
| | Ref-9 | EZ-3 | Ref-10 | EZ-4 | Ref-11 |
| Resin comp.: | | | | | |
| Araldite ® GY-250 | 167.2 | 167.2 | 167.2 | 167.2 | 167.2 |
| Araldite ® DY-E | 31.8 | 31.8 | 31.8 | 31.8 | 31.8 |
| Curing agent comp.: | | | | | |
| EP adduct 1 | — | — | 59.6 | 49.7 | 49.7 |
| EP adduct 2 | 106.1 | 79.6 | — | — | — |
| Jeffamine ® RFD 270 | — | — | 26.8 | 22.3 | 22.3 |
| Amine-1 | — | 45.1 | — | 30.1 | — |
| Amine-6 | — | — | — | — | 28.4 |
| Ancamine ® K 54 | 6.1 | 6.5 | 5.7 | 6.0 | 6.0 |
| Viscosity (10') [Pa · s] | 5.29 | 1.53 | 1.74 | 0.91 | 1.01 |
| Hardness (2 d NK) | 218 | 102 | 160 | 120 | 105 |
| acc. to (4 d NK) | 223 | 114 | 181 | 141 | 123 |
| König [s] (7 d NK) | 232 | 120 | 207 | 151 | 140 |
| (4 w NK) | 231 | 130 | 211 | 170 | 142 |
| Appearance (NK) | nice | nice | nice | nice | nice |
| Hardness (7 d cold) | 139 | 56 | 113 | 52 | 38 |
| acc. to (+2 d NK) | 207 | 106 | 178 | 91 | 83 |
| König (+7 d NK) | 217 | 122 | 192 | 126 | 118 |
| (8°/80%) (+3 w NK) [s] | 216 | 126 | 216 | 155 | 130 |
| Appearance (8°/80%) | matt | l.matt | nice | nice | l.matt |
| Number of markings | 4 (white) | 4 (w) | 1 (w) | 1 (w) | none |

"White" stands for a white discoloration of the marking;
"w" stands for "weak"

The invention claimed is:

1. A curing agent, suitable for curing epoxy resins, comprising an amine of formula (I) and at least one polyamine A which has at least three epoxide group-reactive amine hydrogens,

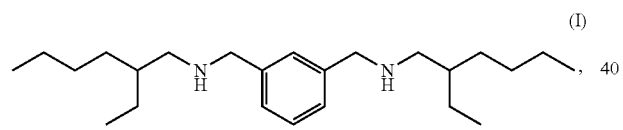

wherein the polyamine A is an adduct with an epoxide.

2. A curing agent, suitable for curing epoxy resins, comprising an amine of formula (I) and at least one polyamine A which has at least three epoxide group-reactive amine hydrogens,

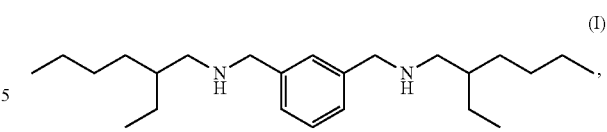

wherein the polyamine A is an adduct with an aromatic monoepoxide.

3. An epoxy resin composition containing at least one epoxy resin and one curing agent suitable for curing epoxy resins, wherein the curing agent comprises an amine of formula (I) and at least one polyamine A which has at least three epoxide group-reactive amine hydrogens,

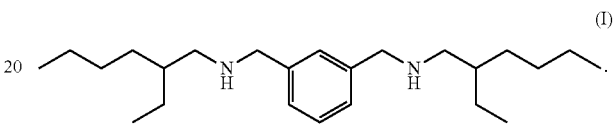

4. The epoxy resin composition according to claim 3, wherein the epoxy resin is a liquid resin that is a glycidyl ether of a bisphenol.

5. A cured composition obtained from curing the composition according to claim 3.

6. An article containing the cured composition according to claim 5.

7. An epoxy resin composition, wherein it is a two-component composition, comprising:

(i) a resin component containing at least one epoxy resin, and (ii) a curing agent component containing an amine of formula (I):

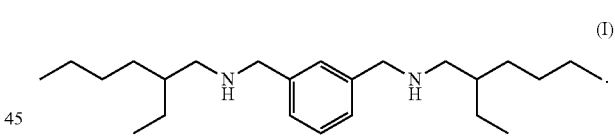

* * * * *